(12) United States Patent
Dubois et al.

(10) Patent No.: US 6,520,176 B1
(45) Date of Patent: Feb. 18, 2003

(54) PORTABLE OXYGEN CONCENTRATOR

(75) Inventors: Anne Dubois, Le Chesnay (FR); Pierre Bodelin, Vanves (FR); Xavier Vigor, Chicago, IL (US)

(73) Assignee: L'Air Liquide, Societe Anonyme a Directoire et Conseil de Surveillance pour l'Etude et l'Exploitation des Procedes Georges Claude, Paris (FR)

( * ) Notice: Subject to any disclaimer, the term of this patent is extended or adjusted under 35 U.S.C. 154(b) by 55 days.

(21) Appl. No.: 09/609,319

(22) Filed: Jun. 30, 2000

(30) Foreign Application Priority Data

May 25, 2000 (FR) .............................................. 0006697

(51) Int. Cl.⁷ ............................................. A61M 15/00
(52) U.S. Cl. .............................. 128/200.24; 128/201.21
(58) Field of Search .................... 128/200.24, 201.21, 128/203.25, 203.26, 203.27, 204.15, 204.17, 204.18, 205.11, 202.26, 204.21, 204.26; 95/96, 130

(56) References Cited

U.S. PATENT DOCUMENTS

| | | | |
|---|---|---|---|
| 4,491,459 A | * 1/1985 | Pinkerton | 96/113 |
| 4,648,888 A | 3/1987 | Rowland | |
| 4,826,510 A | * 5/1989 | McCombs | 128/204.18 |
| 4,971,609 A | 11/1990 | Pawlos | |
| 5,531,807 A | * 7/1996 | McCombs | 55/357 |
| 5,893,275 A | * 4/1999 | Henry | 62/6 |
| 5,893,944 A | * 4/1999 | Dong | 96/114 |
| 5,928,189 A | * 7/1999 | Phillips et al. | 604/65 |
| 5,979,440 A | * 11/1999 | Honkonen et al. | 128/200.24 |
| 6,212,904 B1 | * 4/2001 | Arkharov et al. | 62/47.1 |
| 6,287,366 B1 | * 9/2001 | Derive et al. | 95/100 |
| 6,302,107 B1 | * 10/2001 | Richey et al. | 128/205.11 |
| 6,314,957 B1 | * 11/2001 | Boissin et al. | 128/204.17 |
| 6,346,139 B1 | * 2/2002 | Czabala | 95/130 |
| 6,446,630 B1 | * 9/2002 | Todd, Jr. | 128/204.18 |

FOREIGN PATENT DOCUMENTS

EP          0 860 646          8/1998

* cited by examiner

Primary Examiner—Aaron J. Lewis
Assistant Examiner—Teena Mitchell
(74) Attorney, Agent, or Firm—Young & Thompson

(57) ABSTRACT

An oxygen concentrator portable by a patient, permitting producing a flow of gas containing 50% to 95% of oxygen from air, comprising air compression device, elements for gas separation by adsorption with pressure variations, and electrical energy storage unit keeping its charge for at least 30 minutes, the concentrator having a total weight less than 10 kg. Preferably, the gas separation elements are a PSA system using a zeolite X exchanged with lithium, as the adsorbent.

17 Claims, 3 Drawing Sheets

PORTABLE OXYGEN CONCENTRATOR

FIELD OF THE INVENTION

The invention relates to a portable oxygen concentrator usable in oxygen therapy.

BACKGROUND OF THE INVENTION

Oxygen concentrators using the PSA (Pressure Swing Adsorption) technique are at present very widely used for household oxygen therapy. Nevertheless, their design has a major drawback namely, the lack of portability.

Thus, the existing concentrators require a source of electricity and are moreover too heavy to be transported or carried by the patient.

However, a certain number of patients using oxygen therapy would like to live as "normal" a life as possible, which requires in particular to be able to walk or move more easily.

To give these patients a solution permitting them to make short trips, the documents WO-A-98/58219 and U.S. Pat. No. 5,893,275 propose combining the PSA type concentrator with a liquefier, so as to fill a Dewar (receptacle) that the patient can carry. This solution is in fact more complicated than it appears. Thus, the Dewar for storing the oxygen must be periodically reheated to eliminate any trace of hydrocarbons and water. On the other hand, the adjustment of the liquefaction temperature must be precise so as to avoid at the outset of vaporization for use by the patient, that the initial gas will have a high nitrogen content.

Another solution proposed in U.S. Pat. No. 5,858,062 is to compress a portion of the oxygen leaving the PSA type concentrator to fill a portable cylinder. But this is a costly solution because it is based on the use of an oxygen compressor, and less satisfactory from the point of view of safety, because the patient must manipulate oxygen under pressure.

The present invention thus has for its object to provide patients desiring to have real mobility, an alternative solution that is more simple and more satisfactory as to safety, which is to say improving the known solutions of the prior art.

SUMMARY OF THE INVENTION

The present invention thus relates to an oxygen concentrator portable by a patient, permitting producing a gaseous flow containing 50% to 95% oxygen from air, comprising:

- air compression means to compress the air to a pressure greater than atmospheric pressure (1 bar),
- means for separating gas by adsorption with pressure variations to separate the air compressed by the air compression means and to produce a gas enriched in oxygen, and
- electrical energy accumulating means having a charged life of at least 30 minutes permitting storing and supplying or restoring electricity,
- said concentrator having a total weight less than 10 kg, and
- the weight of the compression means (Mcomp), the weight of the gas separation means (Msieve) and the weight of the energy accumulating means (Mbattery) being such that:

$$0.5 < \frac{Mcomp}{Qp} < 3$$

$$0.15 < \frac{Mbattery}{Qp} < 2$$

$$0.05 < \frac{Msieve}{Qp} < 1$$

wherein Qp is the flow rate of oxygen produced by the concentrator (in l/min) and the weights Mcomp, Mbattery and Msieve are expressed in kg.

According to another aspect, the invention also relates to an oxygen concentrator portable by a patient, permitting producing a gaseous flow containing 50% to 95% of oxygen from air, comprising:

- air compression means to compress the air to a pressure comprised between 1 and 5 bars,
- means for separating gas by adsorption, with pressure variations, comprising several adsorbers each comprising one or several adsorbents operating according to PSA cycles, the duration of each production cycle being less than 30 seconds and at least one adsorbent being a zeolite exchanged with at least one metallic cation selected from lithium, calcium, zinc, copper and their combinations,
- electrical energy accumulation means having a charged life of at least 30 minutes,
- said concentrator having a total weight less than 10 kg, and
- the weight of the compression means (Mcomp), the weight of the gas separation means (Msieve) and the weight of the energy accumulation means (Mbattery) being such that:

$$0.5 < \frac{Mcomp}{Qp} < 3$$

$$0.15 < \frac{Mbattery}{Qp} < 2$$

$$0.05 < \frac{Msieve}{Qp} < 1$$

wherein Qp is the flow rate of oxygen production by the concentrator (in l/min) and the masses Mcomp, Mbattery and Msieve are expressed in kg, said air compression means, said means for separating gas by adsorption and said electric energy accumulating means being disposed within at least one housing, said housing comprising moreover means for controlling or adjusting the operation of the concentrator and at least one system for fastening or carrying the concentrator.

As the case may be, the concentrator of the invention can comprise one or several of the following characteristics:

- Qp is comprised between 0.5 and 4 l/min, preferably between 0.5 and 2 l/min.
- the ratio (Mcomp/Qp) is comprised between 0.5 and 2 kg/(l/min).
- the ratio (Mbattery/Qp) is comprised between 0.15 and 1.2 kg/(l/min).
- the ratio (Msieve/Qp) is comprised between 0.05 and 0.8 kg/(l/min).
- Mcomp+Mbattery+Msieve≦8 kg, preferably Mcomp+Mbattery+Msieve≦5 kg.

the gas separation means comprise several adsorbers each containing one or several adsorbents and operating according to PSA cycles, preferably the duration of each production cycle is less than 30 seconds, preferably less than 20 seconds.

the adsorbent has a granulometry less than 1 mm and/or comprises particles of zeolite X exchanged with at least one metallic cation selected from lithium, calcium, zinc, copper and their combinations, preferably zeolite X having a ratio Si/Al of about 1 to 1.25 and exchanged by at least 80% with lithium cations.

the compression means are adapted or controlled to compress air at a pressure comprised between 1 and 5 bars, preferably between 2.5 and 3.5 bars.

it comprises means for adjusting the temperature permitting adjusting the temperature of the air supply and/or of the adsorbers, to a value comprised between 10 and 60° C.

the controller adjustment means of the operation of the concentrator comprise at least one start/stop means to start or stop the operation of the concentrator, preferably the start/stop means comprises an operating button or a control member actuable by the operator.

the system of securing or carrying the concentrator comprises at least one carrying handle and/or at least one shoulder strap or a belt and/or at least one system of suspending from the belt.

it comprises adjustment means for the flow rate of the gas to be produced by the means for separating gas by adsorption.

BRIEF DESCRIPTION OF THE DRAWINGS

The present invention will now be better understood from the following detailed description given with reference to the accompanying drawings.

DETAILED DESCRIPTION OF THE INVENTION

Contrary to what is said in WO-A-98/58219, the inventors of the present invention have shown that it is in fact possible to produce a really portable concentrator, by combining a certain number of technical advances which will be described below, namely a short production cycle, a small adsorbent granulometry, a "top grade" adsorbent, and the use of a system permitting reducing the flow rate to be produced by the concentrator whilst satisfying the oxygen needs of the patient.

It thus follows that an $O_2$ concentrator should be considered as portable if the two following conditions are satisfied, namely a weight m less than 10 kg, preferably less than 7 kg, and if it can operate on batteries, preferably rechargeable, having a charged life of at least 30 minutes, preferably at least one hour and more preferably at least two hours.

However, the total weight (MTW) of a PSA concentrator depends on the flow rate produced and the performance of the cycle:

the yield $\eta = O_2$ produced/$O_2$ entering productivity per cycle Pcy=$O_2$ produced/cycle/$m^3$ of adsorbent cycle time Tcy=duration of a production cycle (in seconds).

Of course it also depends on the "mass performances" of the different components, for example the ratio between the weight of the compressor and the flow rate of air that it compresses.

The adjustment of a portable concentrator thus passes through a step of establishing the relationships between the performance of the PSA and the weight of the different components. The efficiency of the system will be measured by the weight necessary to produce 1 l/min of oxygen. The system will be lighter the lower this ratio is and/or the lower the required flow rate of oxygen will be.

The principal components whose weight must be reduced are the air compressor, the adsorbent and the battery or the means for accumulating electrical current that are used.

Of course there are other components of the apparatus (external housing, adsorbents of the PSA system, internal tubing, valves . . . ) but their weight is low, or even negligible, relative to that of the principal constituents.

Air Compressor

The flow rate of air (Qa) that is to be supplied by the compressor is $$Q_a = \frac{Q_p}{\eta \times 0.21}$$

in which Qp is the flow rate of produced oxygen (in l/min) $\eta$ is the yield defined above.

However, the best available compressors have a "mass efficiency" comprised between 1 kg for 5 l/min and 1 kg for 10 l /min. These values will therefore permit tracing two curves permitting enclosing the ratio:

Compressor weight/Flow rate of oxygen produced as a function of yield.

Figure 1:
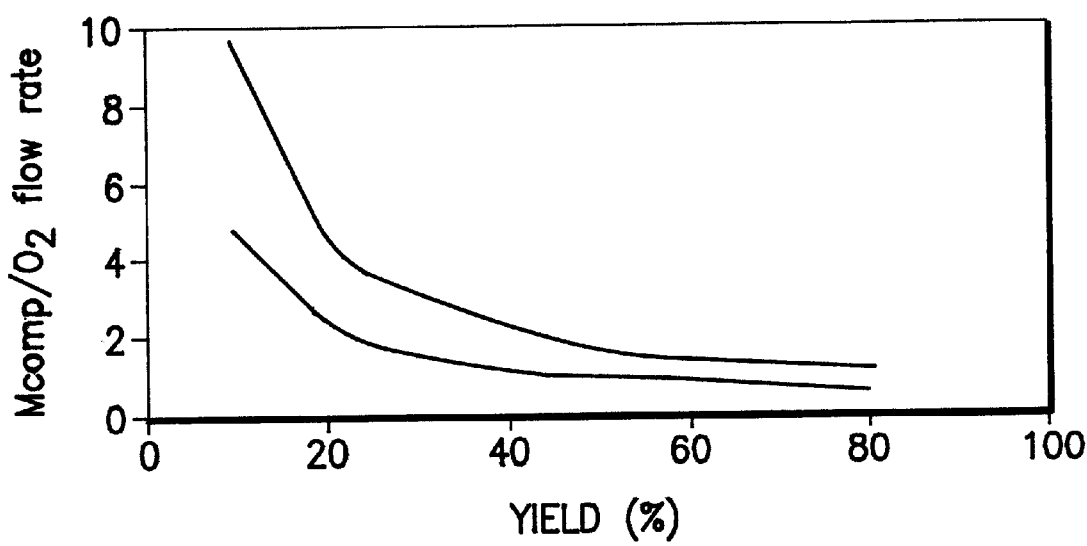
FIG. 1 depicts two curves which represent the ratio of compressor weight to oxygen flow rate as a function of yield.

These curves are schematically shown in FIG. 1.

Having the curves of FIG. 1 and knowing that the yields obtained for a PSA cycle are typically comprised between 30 and 60%, there can be established the following inequality: 0.5 <Mcomp/Qp<3 kg (in kg/(l/min))

Figure 5:
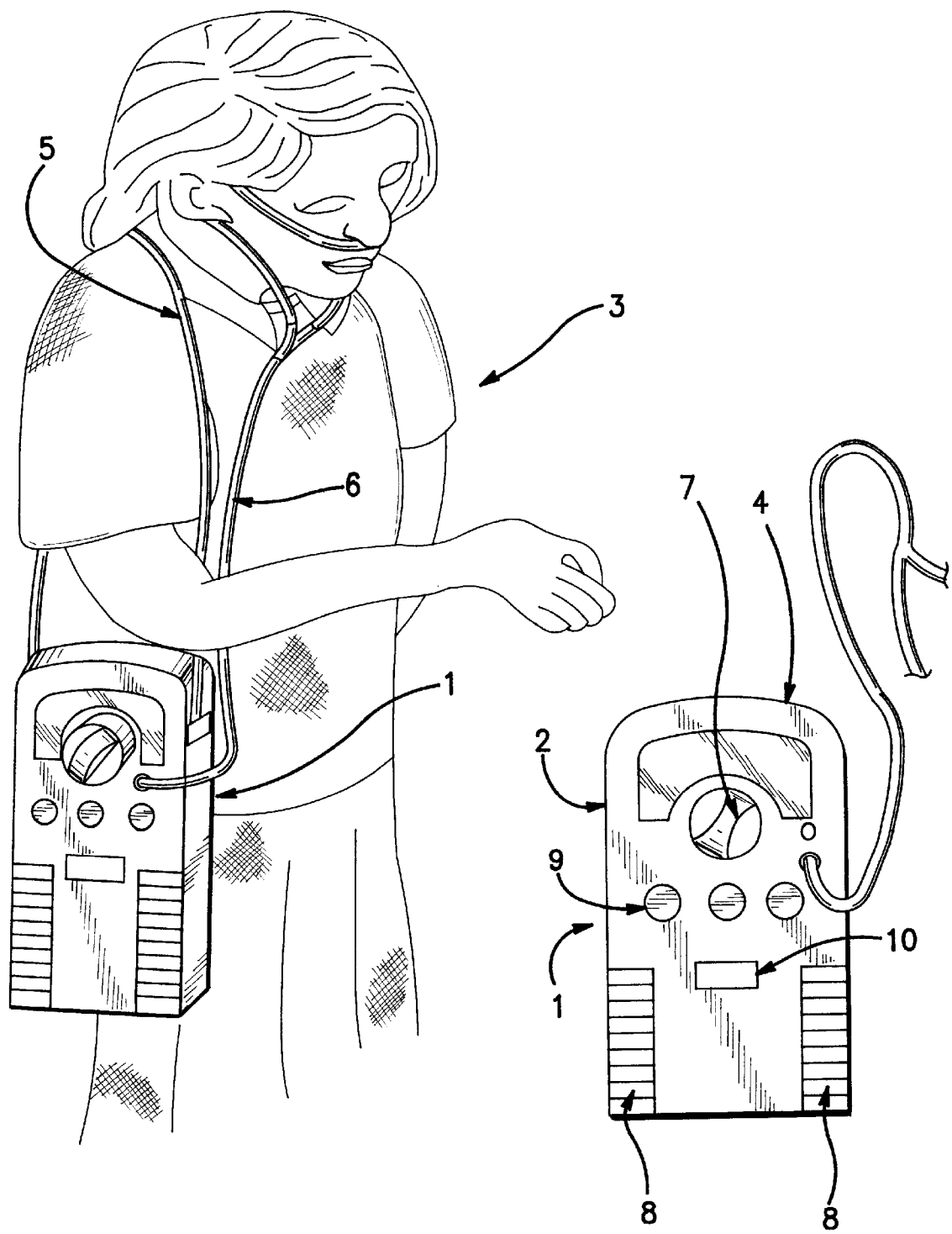
FIG. 5 depicts the portable concentrator according to the invention.

Battery (Reference 8 in FIG. 5)

By analogy, the specific energy Es (in KWh/l of produced oxygen) of a PSA system can be expressed by the following relation:

$$E_s = \frac{k}{\eta + 0.21} \times \log\left(\frac{Ph}{Patm}\right)$$

wherein Ph is the high pressure of the cycle (in bars)

k is comprised between 0.11 and 0.15 according to the compressor

Patm is the atmospheric pressure (1 bar)

For a charged life of 2 hours, the necessary energy (in watts) is therefore expressed by the following relationship:

$$E = \frac{k}{\eta \times 0.21} \times Q_P \times 120 \times \log(Ph/Patm)$$

The high pressure of a PSA system being conventionally comprised between 2.5 and 3.5 bars, and the mass efficiency of the best batteries between 1 kg for 100 watts and 1 kg for 300 watts, there can again be traced two curves (shown in FIG. 2) permitting enclosing the weight ratio battery/O2 flow rate, as a function of yield There is obtained the following inequality:

0.15 <Mbattery/Qp <2 (expressed in kg/(l/min))

Weight of the Adsorbent of the PSA

Similarly, the weight of the adsorbent (Mads) is given by the following relation:

$$Mads = \frac{T_{cy} \times Q_p \times \rho_{ads}}{P_{cy}}$$

wherein $\rho_{ads}$ is the weight per volume of the adsorbent, typically comprised between 0.5 and 0.7 kg/l. Tcy and Pcy are as given above.

The productivity per cycle typically obtained in a PSA cycle is comprised between 0.2 and 0.5 Nl/h/l. The weight of the adsorbent is directly proportional to the cycle time. The reduction of the cycle time can be achieved by a reduction of granulometry of the adsorbent to improve the adsorption kinesis. The cycle time of the medical concentrators is in general less than 25 s thanks to the use of an adsorbent whose mean granulometry is less than 1 mm. They can decrease to several seconds, as indicated by U.S. Pat. No. 5,827,358.

Figure 3:
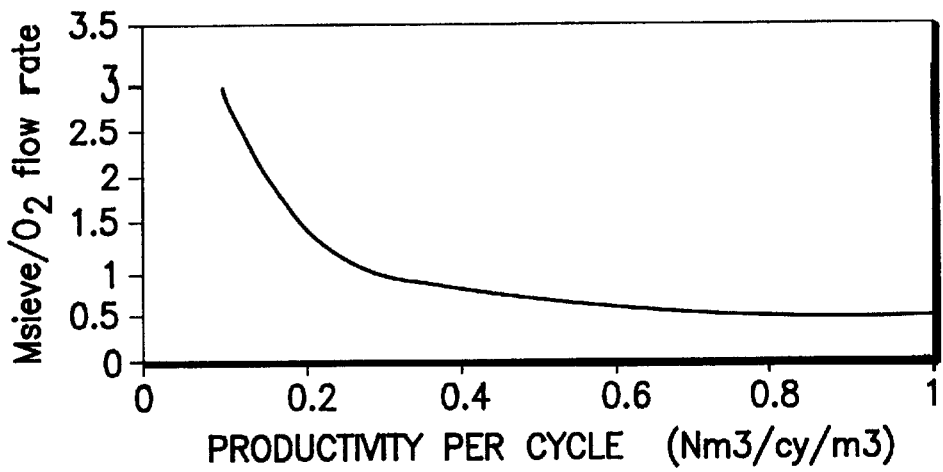
FIG. 3 depicts a curve which represents the ratio of adsorbent weight to oxygen flow rate as a function of productivity per cycle.

There are again obtained two curves permitting enclosing the ratio Mads/O$_2$ flow rate produced as a function of the productivity of the PSA (productivity per cycle), as shown in FIG. 3.

From this there is obtained the following inequality:

0.05<Msieve/Qp<1 (expressed in kg/(l/min))

The rest of the material permitting producing the concentrator has a weight that is relatively less dependent on the production flow rate and can be estimated to be 1 or 2 kg at the most.

Figure 2:
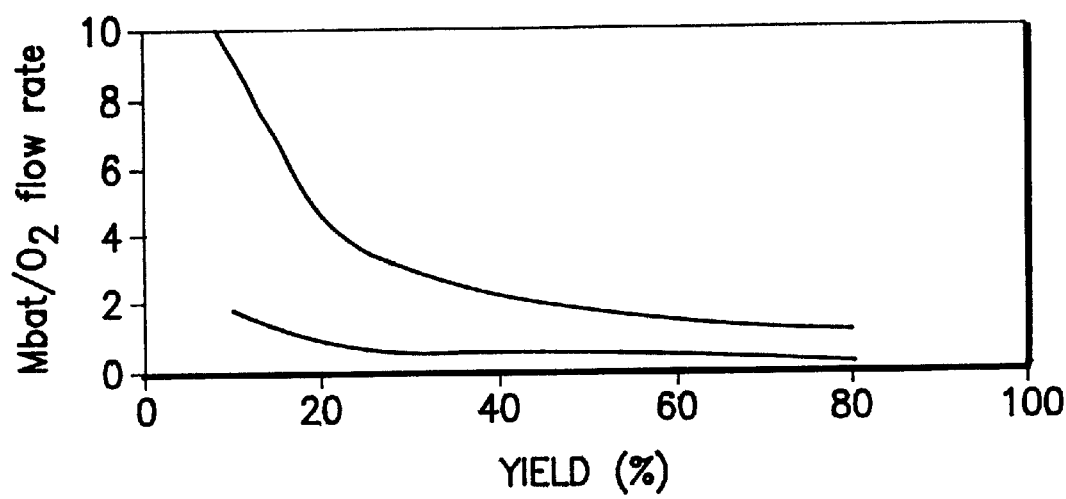
FIG. 2 depicts two curves which represent the ratio of battery weight to oxygen flow rate as a function of yield.

The curves of FIGS. 1 to 3 show three ways of reducing the weight of a concentrator:

reducing the required oxygen flow rate Qp increasing the mass performance of the components: compressor, battery . . .

increasing the performance of the PSA process

The increase of the mass performance of the components is up to the manufacturers. In the present invention, it will suffice to choose components falling within the weight limits described above.

The reduction of the mean required flow rate Qp, to satisfy the oxygen needs of the patient, can be achieved by preferentially adding a system with an economizing valve, permitting delivering oxygen to the patient in a manner synchronized with breathing, and hence to divide the necessary oxygen production of the concentrator by a factor comprised between 1.5 and 6, preferably comprised between 2 and 4.

The usual prescription of gaseous oxygen for a patient undergoing oxygen therapy is comprised between 3 and 6 l/min. The use of such an economizing valve therefore permits reducing the mean flow rate of oxygen that has to be produced by the concentrator, to a value comprised between 0.5 and 4 l/min, preferably between 0.5 and 2 l/min.

The increase of performance of the PSA process is obtained by:

use of a high quality adsorbent, preferably a zeolite X exchanged with lithium, permitting obtaining a yield greater than 45% and a productivity per cycle greater than 0.3 Nm$^3$/h, cycle time less than 20 s, preferably less than 15 s.

In this case, the preceding inequalities thus become:

0.5<Mcomp/Qp<2 (kg/(l/min))

0.1<Mbattery/Qp<1.2 (kg/(l/min))

0.05<Msieve/Qp<0.8 (kg/(l/min))

Under these conditions, it will be seen that the sum of the weights of the different components will be less than 8 kg for mean flow rate values up to 2 l/min.

Generally speaking, as shown in FIG. 5, a portable concentrator 1 according to the invention has a housing 2 of a size and weight permitting the patient 3 to carry it while walking.

Possible systems for securing or carrying the concentrator 1 by the patient 3 are a handle 4 and/or a shoulder strap 5, provided on the concentrator 1 directly or on a bag dimensioned for this purpose, which permit protecting it for all outside uses.

The housing 2 is stable and can rest on any flat surface. It preferably has:

an air outlet enriched in O$_2$, which can be connected to the administration means 6 of the gas to the patient 3;

a start/stop button 9;

an adjustment device 7 for the production flow rate of air enriched in O$_2$;

a screen 10 and/or another system for visualization (luminous signals for example) permitting informing the patient or any other person, of the available adjustments as well as the potential risks and/or misfunctions (residual charge of the battery, misfunction of the compressor, for example);

information labels guaranteeing the quality of the material and if desired the recommendations for its maintenance in good operating condition.

Figure 4:
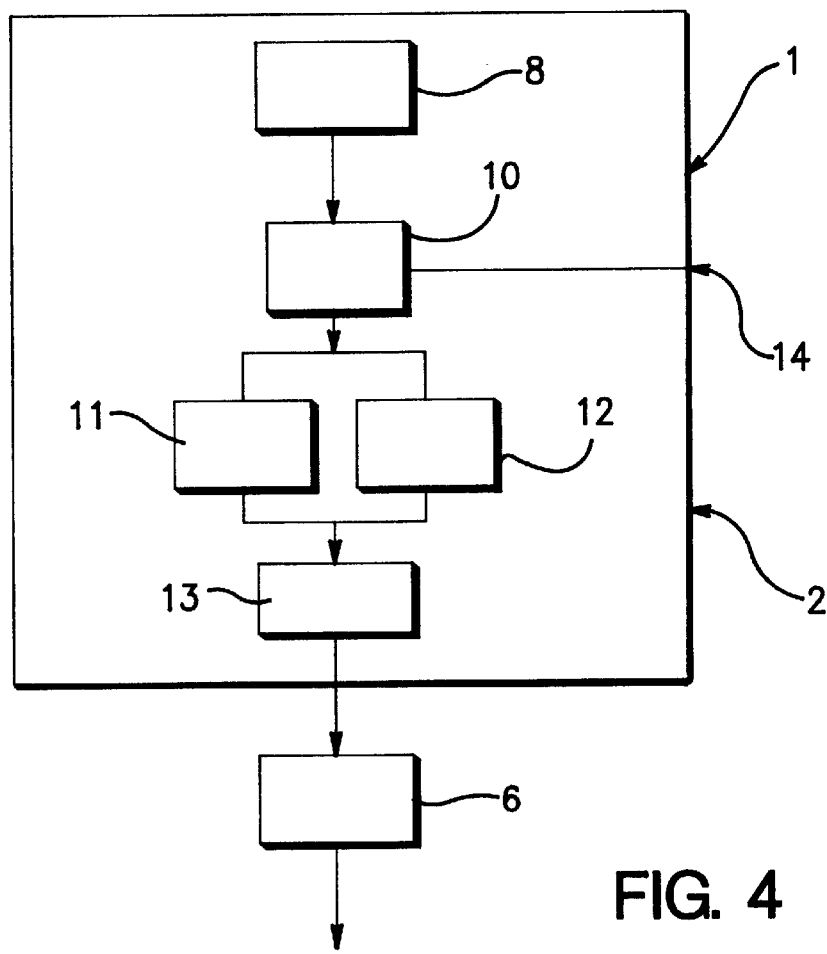
FIG. 4 is a schematic representation of the principle of operation of the portable concentrator according to the invention.

FIG. 4 shows schematically the principle of operation of concentrator 1 according to the invention, comprising an external housing 2 in which are included one or more ambient air inlets 14 (systems of inlets for example) permitting supplying the compression means 10 with gas, and if desired generating an air circulation in the housing 2, gas compression means 10, gas separation means by adsorption with pressure variation (PSA) comprising several adsorbers 11, 12 enclosing adsorbent particles, electrical energy accumulating means 8, a storage 13 for storing air enriched in produced oxygen, and means 6 for supplying air enriched in produced oxygen to the respiratory tract of the patient 3.

Moreover, to the principal elements constituting the concentrator schematically shown in FIG. 4, can be added:

one or several filtration means (dust, antibacterial . . . ) for ambient air and/or air enriched in O$_2$;

an electronic card for controlling the different components and their alarms;

a system for soundproofing the assembly (for example with foam) and more particularly the compressor, via silent blocks for example.

Preferably, the adsorbent used in the psa system is an absorbent, preferably of the zeolite X or LSX type, exchanged by more than 80% with lithium, of the type of those described in EP-A-785020.

What is claimed is:

1. Oxygen concentrator portable by a patient permitting producing a gas flow containing from 50% to 95% of oxygen from air, comprising:
   an air supply;
   air compression means having a weight (Mcomp), and being fluidly connected to the air supply;
   gas separation means for separating gas by adsorption with pressure variation, said gas separation means having a weight (Msieve);
   electrical energy accumulating means having a weight (Mbattery) and a charged life of at least 30 minutes;
   said concentrator having a total weight less than 10 kg; and
   the weight of the air compression means (Mcomp), the weight of the gas separation means (Msieve), and the weight of the electrical energy accumulating means (Mbattery) being such that:

$$0.5 < \frac{Mcomp}{Qp} < 3$$

$$0.15 < \frac{Mbattery}{Qp} < 2$$

$$0.05 < \frac{Msieve}{Qp} < 1$$

wherein Qp is a flow rate of oxygen produced by the concentrator (in l/min) and the weights Mcomp, Mbattery and Msieve are expressed in kg.

2. The oxygen concentrator according to claim 1, wherein Qp is comprised between 0.5 and 4 (l/min).

3. The oxygen concentrator according to claim 2, wherein Qp is comprised between 0.5 and 2 (l/min).

4. The oxygen concentrator according to claim 1, wherein a ratio of the weight of the air compression means to the flow rate of oxygen produced (Mcomp/Qp) is comprised between 0.5 and 2 kg/(l/min).

5. The oxygen concentrator according to claim 1, wherein a ratio of the weight of the electrical energy accumulating means to the flow rate of oxygen produced (Mbattery/Qp) is comprised between 0.5 and 1.2 kg/(l/min).

6. The oxygen concentrator according to claim 1, wherein a ratio of the gas separation means to the flow rate of oxygen produced (Msieve/Qp) is comprised between 0.05 and 0.8 kg/(l/min).

7. The oxygen concentrator according to claim 1, wherein Mcomp+Mbattery+Msieve≦8 kg.

8. The oxygen concentrator according to claim 7, wherein Mcomp+Mbattery+Msieve≦5 kg.

9. The oxygen concentrator according to claim 1, wherein the gas separation means comprise several adsorbers, each containing at least one adsorbent and operating according to pressure swing adsorption cycles, each pressure swing adsorption cycle having a duration of less than 30 seconds.

10. The oxygen concentrator according to claim 9, wherein the adsorbent has a granulometry less than 1 mm and comprises particles of zeolite X exchanged with at least one metallic cation selected from the group consisting of lithium, calcium, zinc, copper and mixtures thereof.

11. The oxygen concentrator according to claim 10, wherein the zeolite X has a ratio of silicon to aluminum (Si/Al) of about 1 to 1.25 and is exchanged by at least 80% with lithium cations.

12. The oxygen concentrator according to claim 9, further comprising means for temperature regulation permitting adjusting the temperature of at least one of the air supply and the adsorbers to a value comprised between 10 and 60° C.

13. The oxygen concentrator according to claim 1, wherein the air compression means are adapted or controlled to compress air from the air supply to a pressure comprised between 1 and 5 bars.

14. The oxygen concentrator according to claim 1, further comprising means for adjusting the flow rate of produced oxygen.

15. Oxygen concentrator portable by a patient permitting producing a gas flow containing 50% to 95% of oxygen from air, comprising:
   air compression means for compressing air to a pressure comprised between 1 and 5 bars, said air compression means having a weight (Mcomp);
   gas separation means for separating gas by adsorption with pressure variation, said gas separation means having a weight (Msieve) and comprising several adsorbers; each adsorber containing at least one adsorbent and operating according to pressure swing adsorption cycles, each cycle having a duration of less than 30 seconds; said at least one adsorbent being a zeolite exchanged with at least one metallic cation selected from the group consisting of lithium, calcium, zinc, copper and mixtures thereof;
   electrical energy accumulating means having a weight (Mbattery) and a charge life of at least 30 minutes;
   said oxygen concentrator having a total weight of less than 10 kg; and
   the weight of the air compression means (Mcomp), the weight of the gas separation means (Msieve) and the weight of the electrical energy accumulating means (Mbattery) being such that:

$$0.5 < \frac{Mcomp}{Qp} < 3$$

$$0.15 < \frac{Mbattery}{Qp} < 2$$

$$0.05 < \frac{Msieve}{Qp} < 1$$

wherein Qp is a flow rate of oxygen produced by the oxygen concentrator (in l/min) and the weights Mcomp, Mbattery and Msieve are expressed in kg;
   said air compression means, said gas separation means for separating gas by adsorption and said electrical energy accumulating means being disposed within at least one housing; and
   said housing comprising control means for controlling operation of the oxygen concentrator and at least one means for securing or carrying the oxygen concentrator.

16. The oxygen concentrator according to claim 15, wherein the control means comprise at least one start/stop button for starting or stopping operation of the oxygen concentrator.

17. The oxygen concentrator according to claim 15, wherein the means for securing or carrying the oxygen concentrator comprise at least one of a carrying handle and shoulder strap.

* * * * *